United States Patent [19]

VandenBerg

[11] Patent Number: Plant 7,518

[45] Date of Patent: May 7, 1991

[54] CHRYSANTHEMUM PLANT NAMED PERLA

[75] Inventor: Cornelis P. VandenBerg, Salinas, Calif.

[73] Assignee: Yoder Brothers, Inc., Barberton, Ohio

[21] Appl. No.: 469,822

[22] Filed: Jan. 24, 1990

[51] Int. Cl.[5] ..... A01H 5/00

[52] U.S. Cl. ..... Plt./77

[58] Field of Search ..... Plt./76, 77

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Perla particularly characterized by its pompon capitulum form; formal decorative capitulum type; white ray floret color; diameter across face of capitulum of 38 to 44 mm when fully opened; photoperiodic flowering response to short days of 50 to 56 days when grown in Salinas, Calif., and 62 to 63 days when grown in Bogota, Colombia; peduncle length of the first lateral of 3 to 10 cm, and of the fourth lateral of 8 to 13 cm, when grown without growth regulator applications, on open, terminal sprays; plant height of 69 to 79 cm when grown as a single stem spray cut mum in Salinas, Calif. with 13 to 14 long days prior to start of short days, and a height of 89 to 109 cm when grown in Bogota, Colombia with 20 to 22 long days prior to start of short days; and excellent tolerance to low night temperatures for bud initiation and flower development.

3 Drawing Sheets

The present invention comprises a new and distinct cultivar of Chrysanthemum, botanically known as *Dendranthema grandiflora*, and referred to by the cultivar named Perla.

Perla, identified as 85-891022, was originated from a cross made by Cornelis P. VandenBerg in a controlled breeding program in Salinas, Calif., in 1985.

The female parent of Perla was the cultivar identified as Statesman, an unpatented cultivar and described as a deep yellow pompon cut spray mum. The male parent of Perla was the cultivar identified as Elfin, disclosed in U.S. Plant Pat. No. 5,810, and described as a light pink small decorative cut spray mum.

Perla was discovered and selected as one flowering plant within the progeny of the stated cross by Cornelis P. VandenBerg in September 1985, in a controlled environment in Salinas, Calif.

The first act of asexual reproduction of Perla was accomplished when vegetative cuttings were taken from the initial selection in November 1986 in a controlled environment in Salinas, Calif., by technicians working under the supervision of Cornelis P. VandenBerg.

Horticultural examination of controlled flowerings of successive plantings has shown that the unique combination of characteristics as herein disclosed for Perla are firmly fixed and are retained through successive generations of asexual reproduction.

Perla has not been observed under all possible environmental conditions. The phenotype may vary significantly with variatio ns in environment such as temperature, light intensity and daylength. For example, plant height will increase with an increased number of long days after planting prior to start of short days. Under low night temperatures (10 degrees Celsius and lower) flowering can be expected to be delayed. Under high temperature (25 degrees Celsius night and 35 degrees Celsius day) flowering can be expected to be delayed and be more uneven than under normal temperatures. Normal temperatures can be described as 15 degrees Celsius minimum night and 25 degrees Celsius maximum day.

The following observations, measurements and comparisons describe plants grown in Salinas, Calif. and Bogota, Colombia, under greenhouse conditions which approximate those generally used in commercial greenhouse practice. The low temperature tolerance was determined in repeated flowerings in Bogota, Colombia.

The following traits have been repeatedly observed and are determined to be basic characteristics of Perla, which, in combination, distinguish this Chrysanthemum as a new and distinct cultivar:

1. Pompon capitulum form.
2. Formal decorative capitulum type.
3. White ray floret color.
4. Diameter across face of capitulum of 38 to 44 mm when fully opened.
5. Flowering response in Salinas under normal temperatures is 50 to 56 days after start of short days. Flowering response in Bogota, Colombia under minimum 7 degrees Celsius night and maximum 29 degrees Celsius days is 62 to 63 days after start of short days.
6. Peduncle length of the first lateral at flowering after removing the apical bud without growth regulator applications is 3 to 8 cm when grown in Salinas, Calif., and 3 to 10 cm when grown in Bogota, Colombia. Peduncle length of the fourth lateral at flowering is 8 to 13 when grown in Salinas, and 8 to 10 cm when grown in Bogota.
7. Plant height is 69 to 79 cm when grown in Salinas with 13 to 14 long days prior to start of short days, and 89–109 cm when grown in Bogota with 20 to 22 long days prior to start of short days.
8. Excellent tolerance to low night temperatures for bud initiation and flower development. Average minimum low night temperatures in our Bogota trails ranged from 7 to 8.5 degrees Celsius.

The above measurements represent repeated flowerings over a period of a minimum of two years.

The accompanying photographic drawings show typical inflorescence and leaf characteristics of Perla, with the colors being as nearly true as possible with illustrations of this type.

Sheet 1 is a color photograph of Perla grown as a single stem cut spray mum.

Sheet 2 is a black and white photograph of three views of the inflorescence of Perla.

Sheet 3 is a black and white photograph showing the upper and under sides of the leaves of Perla at three stages of development (mature, intermediate and immature).

Of the cultivars known to the inventor, the most similar in comparison to Perla is the cultivar Nimba, a white small decorative spray cut mum disclosed in U.S. Plant Pat. No. 6,947. Reference is made to attached Chart A, which compares certain characteristics of Perla to the same characteristics of Nimba. Because of the poor low night temperature performance of Nimba, this cultivar is not being grown in Bogota, and Chart A accordingly shows no measurements of Nimba from that location.

Similar traits are ray floret color, capitulum form and type, spray formation, and diameter of capitulum. Perla has shorter peduncles, shorter plant height, comparable flowering response and much better low night temperature tolerance than Nimba.

In the following description color references are made to The Royal Horticultural Society Colour Chart. The clear white ray floret color of Perla is not represented in the RHS colour chart. The color values were determined on plant material grown in Salinas, Calif. on July 14, 1989.

Classification:

*Botanical.*—*Dendranthema grandiflora* cv Perla.

*Commercial.*—Pompon formula decorative.

INFLORESCENCE

A. Capitulum:

*Form.*—Pompon.

*Type.*—Formal decorative.

*Diameter across face.*—38 to 44 mm when fully opened.

B. Corolla of Ray Florets:

*Color (general tonality from a distance of three meters).*—White.

*Color (upper surface).*—White.

*Color (under surface).*—White.

*Center of young flowers.*—155A.

*Shape.*—Straight, oblong, ribbed, strongly concave.

C. Corolla of Disc Floret:

*Color (mature).*—Closet to 14A.

*Color (immature).*—Closet to 145B.

D. Reproductive organs:

*Androecium.*—Prenset on disc florets only; very few disc florets; no pollen.

*Gynoecium.*—Present on both ray and disc florets.

PLANT

A. General appearance:

*Height.*—69 to 79 cm when grown as a single stem cut mum with 13 to 14 long days prior to start of short days in Salinas, Calif.; 89 to 109 cm when grown as a single stem cut mum with 20 to 22 long days prior to start of short days in Bogota, Colombia.

B. Foliage:

*Color (upper surface).*—147A.

*Color (under surface).*—147B.

*Shape.*—See photograph.

CHART A

COMPARISON OF PERLA AND NIMBA

| CHARACTERISTIC | PERLA | NIMBA |
|---|---|---|
| Ray floret color | White | White |
| Capitulum form | Pompon | Pompon |
| Capitulum type | Formal decorative | Formal decorative |
| Spray formation | Terminal | Terminal |
| Peduncle length | | |
| 1st lateral, Salinas | 3 to 8 cm | 10 to 13 cm |
| 4th lateral, Salinas | 8 to 13 cm | 13 to 18 cm |
| 1st lateral, Bogota | 3 to 10 cm | Not available |
| 4th lateral, Bogota | 8 to 10 cm | Not available |
| Diameter across face of capitulum | 38 to 44 mm | 38 to 44 mm |
| Plant height | | |
| 13–14 long days, Salinas | 69 to 79 cm | 89 to 97 cm |
| 20–22 long days, Bogota | 89 to 109 cm | Not available |
| Flowering response period | | |
| in Salinas | 50 to 56 days | 51 to 53 days |
| in Bogota | 62 to 63 days | Not available |
| Low night temperature tolerance | Excellent | Poor |

COMPARISONS MADE OF PLANTS GROWN AS SINGLE STEM SPRAY CUT MUMS IN SALINAS, CALIFORNIA, AND CHARACTERISTICS OF PLANTS OF PERLA GROWN IN BOGOTA, COLOMBIA

I claim:

1. A new and distinct Chrysanthemum plant named Perla, as described and illustrated.

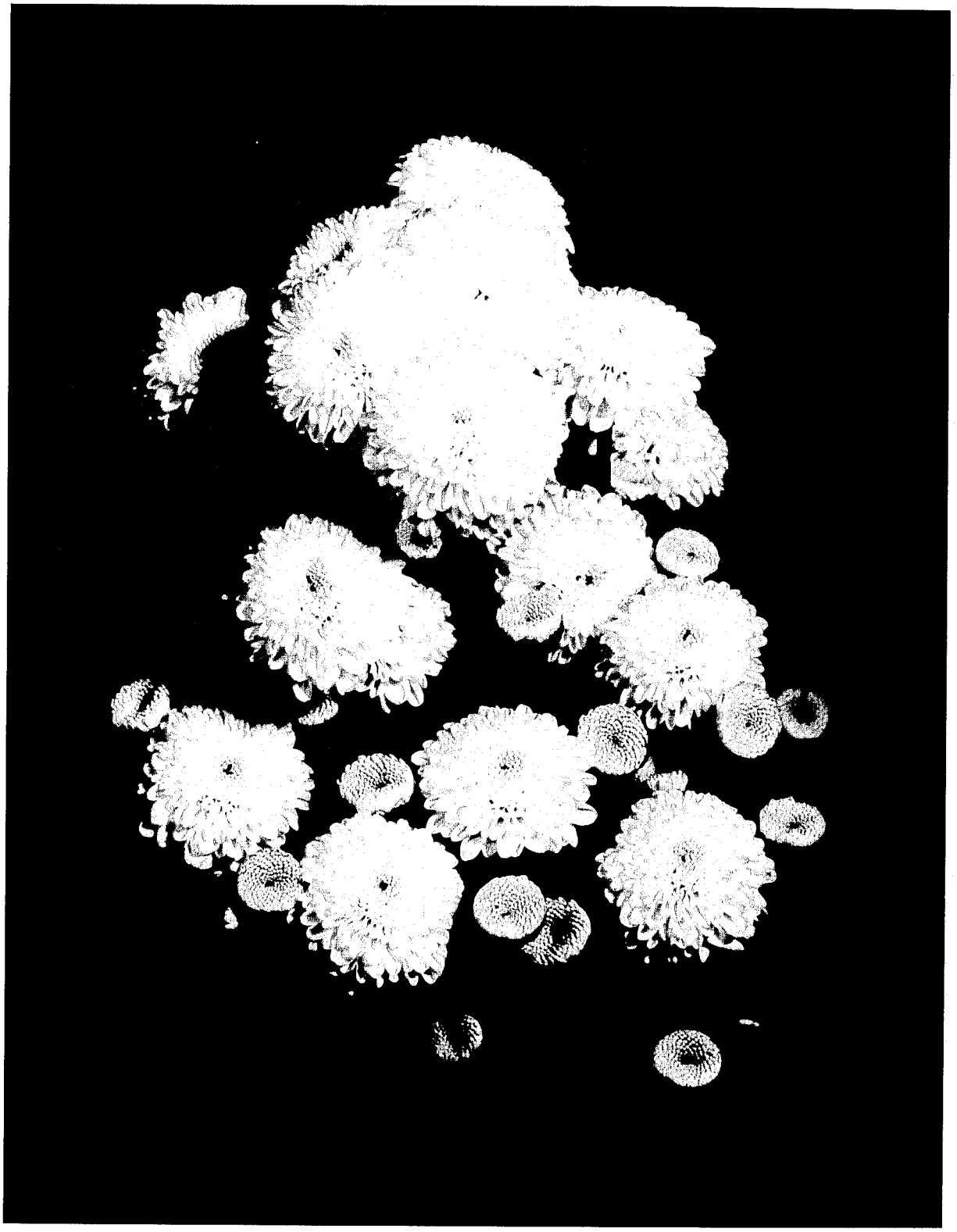

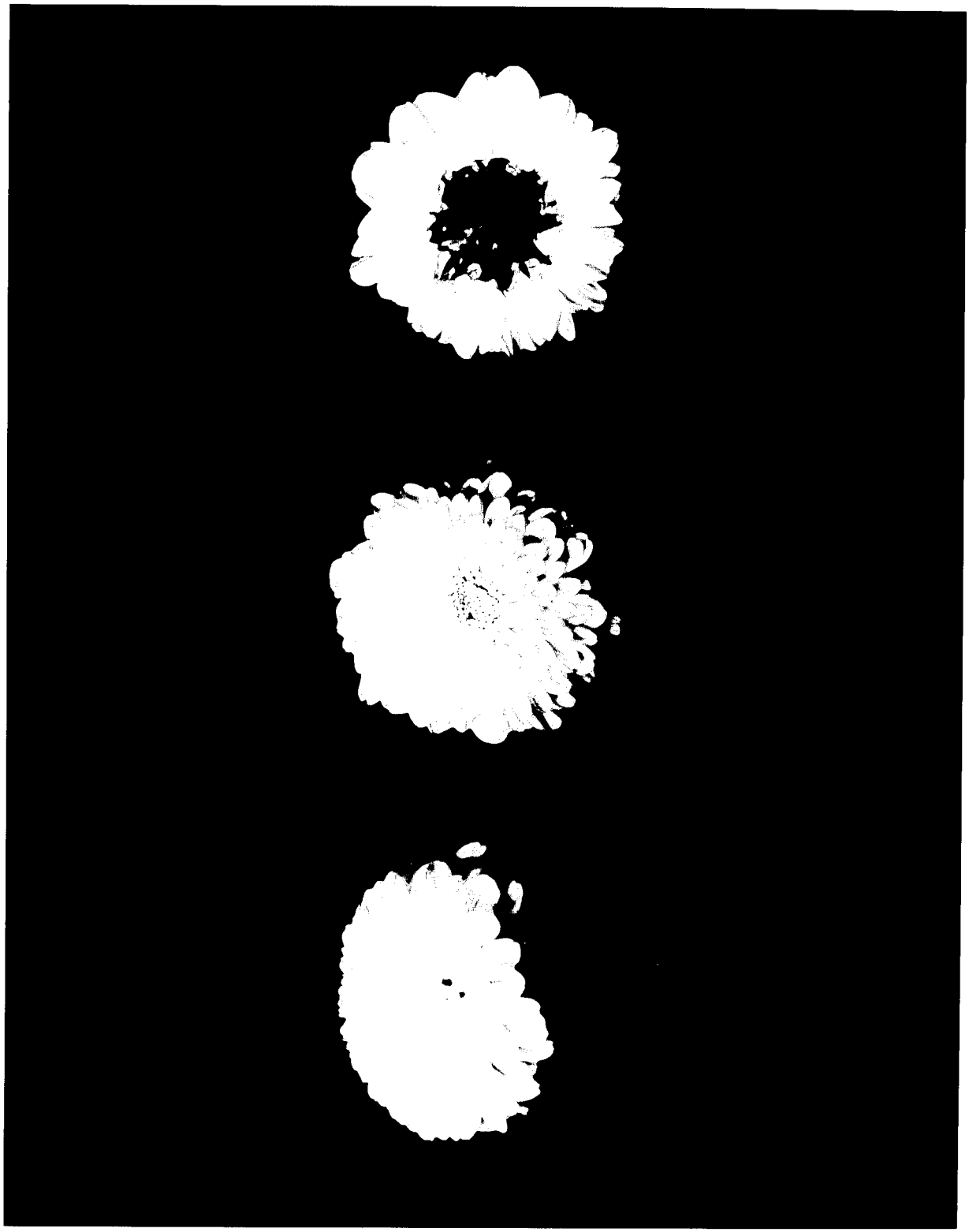

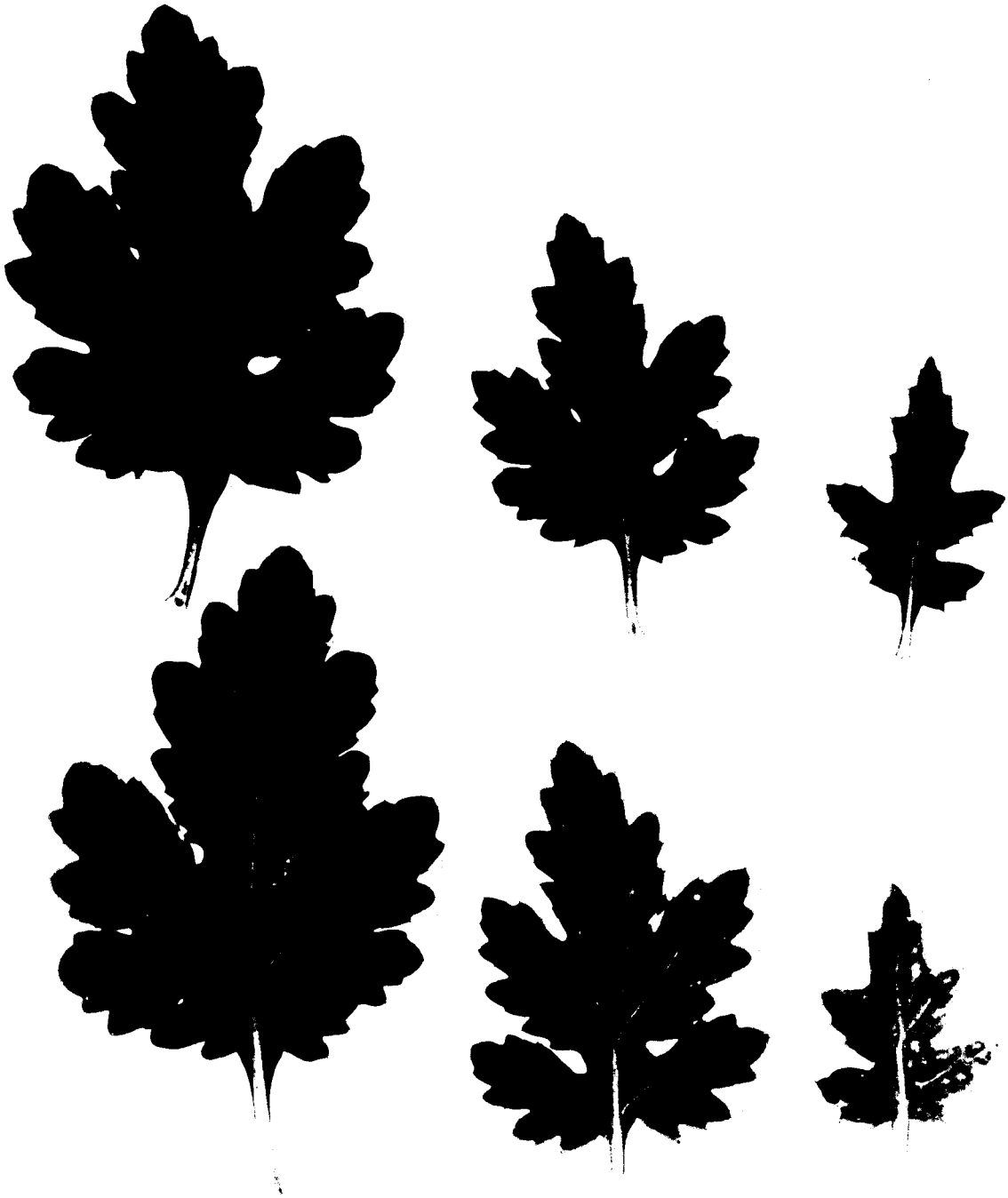

* * * * *